United States Patent
Singh

(10) Patent No.: US 7,714,083 B2
(45) Date of Patent: May 11, 2010

(54) RECYCLE OF HYDROCARBON GASES FROM THE PRODUCT TANKS TO A REACTOR THROUGH THE USE OF EJECTORS

(75) Inventor: Diwaker Singh, Singapore (SG)

(73) Assignee: ExxonMobil Chemical Patents Inc., Houston, TX (US)

( * ) Notice: Subject to any disclaimer, the term of this patent is extended or adjusted under 35 U.S.C. 154(b) by 1038 days.

(21) Appl. No.: 11/370,949

(22) Filed: Mar. 8, 2006

(65) Prior Publication Data
US 2007/0213478 A1   Sep. 13, 2007

(51) Int. Cl.
 *B01J 8/18*      (2006.01)
 *C08F 2/00*     (2006.01)
 *C08F 210/00*  (2006.01)

(52) U.S. Cl. .............. 526/68; 526/69; 526/70; 526/348; 422/139

(58) Field of Classification Search ............. 422/139; 526/68, 69, 70, 348
See application file for complete search history.

(56) References Cited

U.S. PATENT DOCUMENTS

| | | | |
|---|---|---|---|
| 4,543,399 A | 9/1985 | Jenkins, III et al. | |
| 4,588,790 A | 5/1986 | Jenkins, III et al. | |
| 4,640,963 A | * | 2/1987 | Kreider et al. ............... 526/67 |
| 5,028,670 A | 7/1991 | Chinh et al. | |
| 5,317,036 A | 5/1994 | Brady, III et al. | |
| 5,352,749 A | 10/1994 | DeChellis et al. | |
| 5,405,922 A | 4/1995 | DeChellis et al. | |
| 5,436,304 A | 7/1995 | Griffin et al. | |
| 5,453,471 A | 9/1995 | Bernier et al. | |
| 5,462,999 A | 10/1995 | Griffin et al. | |
| 5,616,661 A | 4/1997 | Eisinger et al. | |
| 5,668,228 A | 9/1997 | Chinh et al. | |
| 6,910,343 B2 | 6/2005 | Ozaki et al. | |

FOREIGN PATENT DOCUMENTS

| EP | 0 549 252 A | 6/1993 |
|---|---|---|
| EP | 0 735 058 A | 10/1996 |

* cited by examiner

*Primary Examiner*—William K Cheung

(57) ABSTRACT

The present invention provides a method and apparatus for separating unreacted monomer from a polymerization process effluent stream, wherein the effluent stream comprises unreacted monomer and polymer particles. The method comprises passing the effluent stream of a fluidized-bed reactor into at least one container, feeding a high-pressure olefin through an ejector, and vacuuming at least a portion of the effluent stream from the at least one container through the ejector. The apparatus comprises a fluidized-bed reactor having a first conduit connected to a first tank, an ejector having a second conduit connected to the first tank, and a third conduit connected to the fluidized-bed reactor.

40 Claims, 2 Drawing Sheets

RECYCLE OF HYDROCARBON GASES FROM THE PRODUCT TANKS TO A REACTOR THROUGH THE USE OF EJECTORS

FIELD OF THE INVENTION

The present invention relates to the field of separating polymer particles from a fluid stream and to a method and apparatus for separating polymer particles from unreacted monomer using an ejector.

BACKGROUND OF THE INVENTION

In a typical fluidized-bed polymerization system, monomer (and possibly co-monomer, liquid diluents, and/or catalyst and possibly co-catalyst) is fed into one or more reactors. The monomer (and possibly co-monomer) reacts to produce a product effluent containing polymer particles of various sizes enriched with dissolved diluents (if used), unreacted gaseous monomer, unreacted gaseous co-monomer (if used), catalyst and co-catalyst (if used). The effluent is removed from the reactor, and typically contains between about 2 to about 20 weight % gases, between about 0 to about 10 weight % liquids, and between about 70 to about 98 weight % solids. For economical operation of this process, the unreacted monomer (and possibly co-monomer and/or diluent) is typically separated from the polymer particles and then returned to the reactor(s).

As used in the industry, the term "polymer particle(s)" typically includes solid polymer particles and/or polymer particles that are enriched with dissolved diluents.

Conventional methods of making polymer particles and methods of separating the polymer particles from fluids are generally disclosed in, inter alia, U.S. Pat. Nos. 4,543,399; 4,588,790; 5,028,670; 5,317,036; 5,352,749; 5,405,922; 5,436,304; 5,453,471; 5,462,999; 5,616,661; and 5,668,228; all of which are fully incorporated herein by reference.

For example, U.S. Pat. No. 5,028,670, assigned to BP Chemicals Limited, discloses a process and apparatus for the gas-phase polymerization of olefins in a fluidized-bed reactor maintained at a temperature T1. A gaseous reaction mixture comprising olefins to be polymerized passes through the reactor and is recycled to the reactor by means of a recycling line comprising successively a first heat transfer means, a compressor, and a second heat transfer means. A readily volatile liquid hydrocarbon is introduced into the inlet of the first heat transfer means or into the recycling line, upstream and in the vicinity of the first heat transfer means. The first heat transfer means cools the gaseous reaction mixture to a temperature T2, below T1, while volatilizing the readily volatile hydrocarbon and without condensing a constituent of the gaseous reaction mixture. The second heat transfer means cools the gaseous reaction mixture to a temperature T3, below T2, in order to maintain the fluidized-bed at the desired temperature T1.

In another example, U.S. Pat. No. 5,436,304, assigned to Exxon Chemical Patent Inc., discloses polymerizing or copolymerizing alpha-olefins either alone or in combination with one or more other alpha-olefins in a gas phase reactor having a fluidized bed and a fluidizing medium such that the fluidizing medium entering the reactor comprises a gas and a liquid phase. During reactor operation, the product is removed from the reactor through a discharge system. The discharge of polymer product is preferably followed by separation of fluids from the polymer product. These fluids may be returned to the recycle stream line as a gas and/or as a condensed liquid.

In a still further example, U.S. Pat. No. 4,543,399, assigned to Union Carbide Corporation, discloses a process for increasing the space time yield of polymer production in a fluidized bed reactor employing an exothermic polymerization reactor by cooling the recycle stream to below its dew point and returning the resultant two-phase fluid stream to the reactor to maintain the fluidized bed at a desired temperature above the dew point of the recycle stream. On discharge of particulate polymer product from the reactor, it is desirable and preferable to separate fluid from the product and to return the fluid to a recycle line. In one such system, fluid and product leave the reactor and enter a product discharge tank. Positioned above and below the product discharge tank are at least two conventional valves, one being adapted to provide passage of product into a product surge tank. The other valve releases fluid to second surge tank. Fluid from the second surge tank is directed through a filter absorber and then through a compressor and into the recycle line.

Additional references of interest include: U.S. Pat. No. 4,543,399 to Jenkins et al.; U.S. Pat. No. 4,588,790 to Jenkins et al.; U.S. Pat. No. 5,028,670 to Chinh; U.S. Pat. No. 5,317,036 to Brady et al.; U.S. Pat. No. 5,352,749 to DeChellis; U.S. Pat. No. 5,405,922 to DeChellis; U.S. Pat. No. 5,436,304 to Griffin; U.S. Pat. No. 5,453,471 to Bernier; U.S. Pat. No. 5,462,999 to Griffin; U.S. Pat. No. 5,616,661 to Eisinger; U.S. Pat. No. 5,668,228 to Chinh; and U.S. Pat. No. 6,910,343 to Ozaki.

The use of a mechanical compressor(s) to aid in the recycling of unreacted monomer from the product tanks to the reactor is generally undesirable in the foregoing processes, as these mechanical compressors have relatively high capital expense and operating costs. Additionally, the pressure in the tanks is generally close to the reactor pressure for a significant amount of the discharged gases to flow unaided from the product tanks to the reactor. Accordingly, there is a need for a process that can separate polymer particles from fluids and recycle, without mechanical compression, a significant portion of the fluids. The present invention provides a solution to the aforementioned problem in that the pressure of fresh monomer delivered to the reactor is generally higher than what is necessary to run the reactor. Accordingly, high pressure monomer may be used as the motive fluid to an ejector to create low pressure in the product tank(s). The lower pressure in the tanks would eject gases, cause dissolved fluid in the polymer product to evolve and suck the free and evolved gases to the throat of one or more ejectors. The mixed stream of motive monomer and ejected monomer may be fed to the reactor without additional compression. In this manner, less energy is required to recycle monomer from the product tanks to the reactor than would be used if a compressor system were used to recycle the monomer.

SUMMARY OF THE INVENTION

The present invention provides a method of separating unreacted monomer from a polymerization process effluent stream having unreacted monomer and polymer particles. The method comprises passing the effluent stream of a fluidized-bed reactor into at least one container; feeding a first high-pressure olefin through an ejector; and vacuuming at least a portion of the effluent stream from the at least one container through the ejector.

In another embodiment, the present invention provides a method of separating unreacted monomer from a polymerization process effluent stream having unreacted monomer and polymer particles. The method comprises passing the effluent stream of a fluidized-bed reactor through a first conduit and a first valve into a product chamber tank; passing a first portion of the effluent stream from the product chamber tank through a second conduit and a second valve into a product blow tank; feeding a first high-pressure olefin into the inlet of an ejector, having an inlet, an outlet, and an alternate inlet port; vacuuming a second portion of the effluent stream from the product chamber tank through a third conduit and a third valve to the alternate inlet port of the ejector; vacuuming a third portion of the effluent stream from the product blow tank through a fourth conduit and a fourth valve to the alternate inlet port of the ejector; passing a fourth portion of the effluent stream from the product blow tank through a fifth conduit and a fifth valve to a product purge bin; and passing an exit stream from the outlet of the ejector into the fluidized-bed reactor.

In a further embodiment, the present invention provides an apparatus for separating unreacted monomer from a polymerization process effluent stream, wherein the apparatus comprises a fluidized-bed reactor having a first conduit and a first valve connected to a first tank, an ejector having a second conduit and a second valve connected to the first tank, and a third conduit and a third valve connected to the fluidized-bed reactor.

In a still further embodiment, the present invention provides a method for retrofitting a polymerization process. The process having at least a fluidized bed reactor, an effluent stream comprising unreacted monomer and polymer particles, one or more product tanks, and a compressor. The method comprises effectively limiting the compressor; vacuuming at least a first portion of the effluent stream from the at least one tank into an ejector, wherein the ejector is driven by a high-pressure gaseous olefin; and recycling the vacuumed portion of the effluent stream from the ejector to a fluidized-bed reactor.

Other features and advantages of the present invention will be apparent to those of ordinary skill in the art upon reference to the following detailed description and the accompanying drawings.

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The embodiments and figures discussed herein are merely illustrative and are not intended to limit the scope of the invention.

As used herein, the term "polymer particle(s)" includes solid polymer particles and/or polymer particles that are enriched with dissolved diluents. The term "diluent(s)" refers to total diluent within the referenced system, including gaseous diluents, liquid diluents, and dissolved diluents entrained within the polymer particles. The terms "liquid diluent(s)" and "gas(eous) diluent(s)" refer to diluent(s) that are outside of the polymer particles. The given weight and volume percent of liquids refer to the total weight or volume percent of the liquid in the referenced system, including any dissolved diluent within the polymer particles and the liquid diluent. When the term "monomer" is used, it is to be understood that the presence of co-monomer or co-monomers is optional and acceptable. When the term "catalyst" is used, it is to be understood that the presence of co-catalyst or co-catalysts is optional and acceptable. The terms "fluid" and "fluids" include gaseous materials and liquid materials, whether or not entrained in the polymer particles. Finally, for the purposes of this disclosure, it is to be understood that when weight or volume percents are given, they are percents relative to the disclosed components of that system. In this manner, for example, when the given weight or volume percent totals 100%, an undisclosed amount of other materials, such as for example entrained impurities, may be present.

Figure 1:
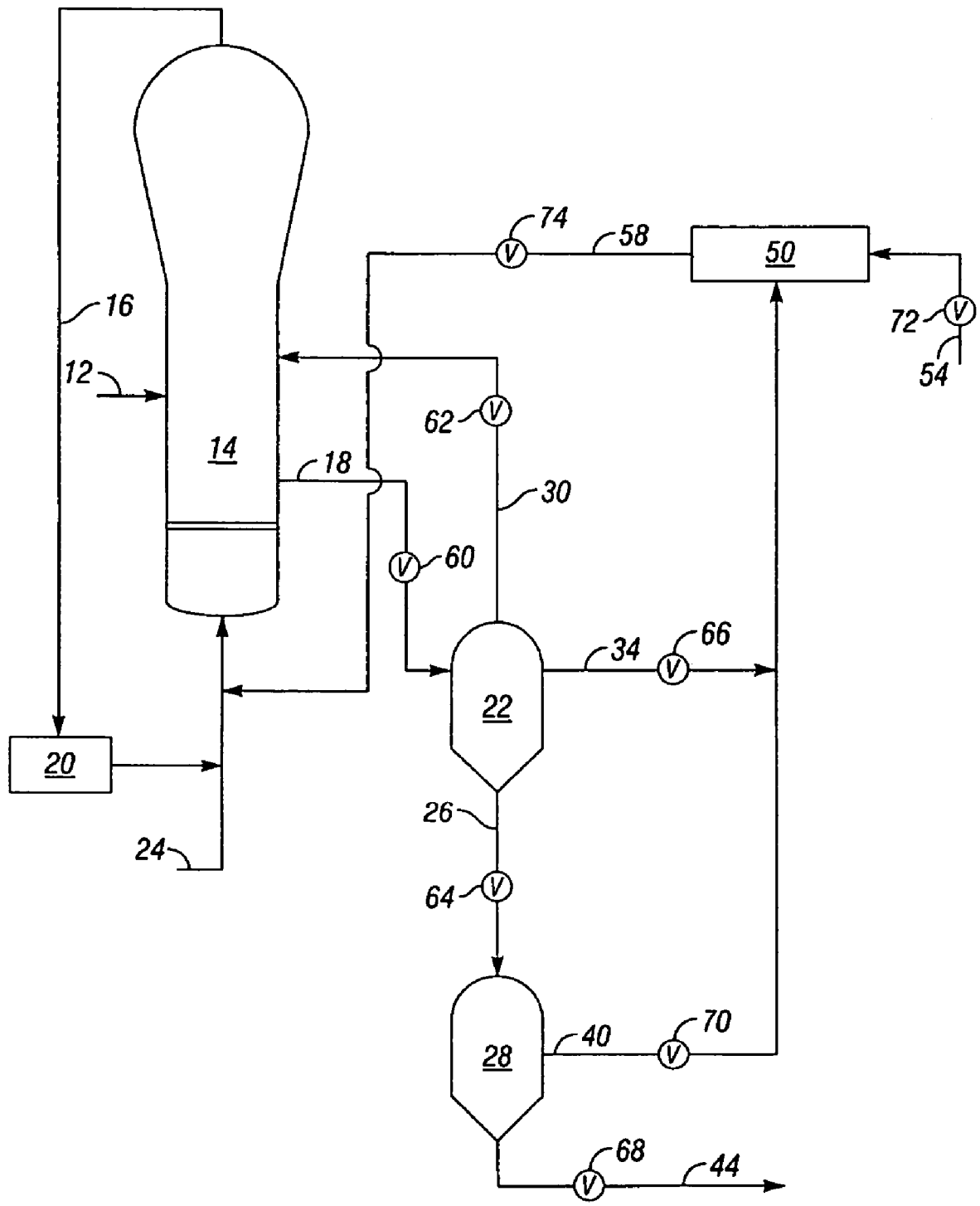
FIG. 1 illustrates a method of separating fluids from a polymerization reactor effluent stream, in accordance with one embodiment of the present invention.

FIG. 1 illustrates a method for separating gaseous monomer and liquid diluents from polymer particles within an effluent stream 18, and recycling the gaseous monomer and liquid diluents into a reactor 14. Suitable reactors 14 for use according to the present invention include any reactor known in the art to be used for fluidized bed polymerization of olefins, especially ethylene, propylene, or mixtures of these with other alpha olefins. Examples of such reactors, as well as corresponding reaction chemistry, are described in, inter alia, U.S. Pat. Nos. 4,543,399; 4,588,790; 5,028,670; 5,317,036; 5,352,749; 5,405,922; 5,436,304; 5,453,471; 5,462,999; 5,616,661; and 5,668,228; all of which are fully incorporated herein by reference. Catalyst is fed into the reactor 14 through the catalyst feed stream 12. A makeup stream 24 containing any combination of gaseous monomer, liquid monomer, gaseous diluents, and/or liquid diluents is optionally fed to the reactor 14. During operation, the fluid level of the reactor 14 may optionally be controlled by the amount of fluid fed through the makeup stream 24. Fluidized bed reactors are typically operated at a pressure between about 2000 kPag to about 3000 kPag, preferably between about 2000 kPag to about 2400 kPag, more preferably between about 2050 kPag to about 2200 kPag. The temperature of a fluidized bed reactor typically ranges from between about 70° C. to about 120° C., preferably between about 70° C. to about 115° C., and most preferably between about 75° C. to about 110° C.

When a sufficient amount of polymer particles are produced, an effluent stream 18 is discharged from the reactor 14. The effluent stream 18 contains unreacted gaseous monomer, polymer particles, and, optionally, diluents. The effluent stream 18 contains between about 70 weight % to about 98 weight % polymer particles, between about 85 weight % to about 95 weight % polymer particles, or between about 90 weight % to about 95 weight % polymer particles. The effluent stream 18 also contains between about 2 weight % to about 20 weight % gaseous monomer, between about 4 weight % to about 15 weight % gaseous monomer, or between about 4 weight % to about 8 weight % gaseous monomer. The effluent stream 18 further contains between about 0 weight % to about 10 weight % diluents, between about 0 weight % to about 7 weight % diluents, or between about 0.5 weight % to about 5 weight % diluents.

A circulation stream 16 may be employed to cycle gaseous monomer and gaseous diluents from the top of the reactor 14 to the bottom of the reactor 14. Further, a circulation unit 20 may be used to blow the gaseous monomer and gaseous diluents, and optionally to remove heat from the gaseous monomer and gaseous diluents. The circulation unit 20 may include a blower and/or a heat exchanger. Preferably, the blower is a centrifugal compressor. In an embodiment, the heat exchanger removes an amount of heat such that the phase of the gas going through it does not change. In another embodiment, the heat exchanger removes enough heat from the gas going through it that at least a portion of the gas condenses.

When a sufficient amount of polymer particles are produced, the effluent stream 18 is discharged from the reactor 14 via a first conduit through a first valve 60 and into a product chamber tank 22. In an alternate embodiment, two product chambers may be operated in sequence. In a further embodiment, four product chamber tanks may be operated in pairs and/or in series. The first valve 60 is closed after the product chamber tank 22 contains a sufficient amount of the effluent stream 18. The pressure of the product chamber tank 22 typically ranges from about 600 kPag to about 2450 kPag; in another embodiment the pressure ranges from about 700 kPag to about 2200 kPag; and in a further embodiment the pressure ranges from about 800 kPag to about 2150 kPag. The contents of the product chamber tank 22 are permitted to settle or equalize by closing the first valve 60, closing the second valve 62 and keeping closed the third valve 64 and the fourth valve 66. During settling the polymer particles will tend to fall to the bottom of the product chamber tank 22, while the fluid unreacted material will tend to rise to the top of the product chamber tank 22. The settling or equalization time varies from about 1 second to about 5 minutes, preferably from about 1 second to about 1 minute, and more preferably from about 1 second to about 30 seconds. Also during settling in the product chamber tank 22, gaseous monomer and liquid and/or gaseous diluents may be allowed to flow back into the reactor 14 from the product chamber tank 22 through a second conduit 30 by opening a second valve 62. After the settling period, the polymer particles, liquid and/or gaseous diluents, and accompanying gaseous monomers are transferred via a third conduit 26 through a third valve 64 into a product blow tank 28. In an alternate embodiment, the polymer particles, liquid and/or gaseous diluents, and accompanying gaseous monomers are transferred via the third conduit 26 and the opened third valve 64 into the product blow tank 28 while the product chamber tank 22 is undergoing settling or equalization. Most of the gaseous monomer and liquid and/or gaseous diluents are either pulled through a fourth conduit 34 by an ejector 50 when a fourth valve 66 is opened, or escape with the polymer particles through the third conduit 26 and into the product blow tank 28. In one embodiment, about 70 volume % to about 100 volume %, preferably about 80 volume % to about 100 volume %, and more preferably about 90 volume % to about 100 volume % of the gaseous monomer and/or gaseous diluents within the product chamber tank 22 are pulled through the opened fourth valve 66 and the fourth conduit 34 by the ejector 50. Further, polymer particles and liquid and/or gaseous diluents may escape from the product chamber tank 22 into the ejector 50 via the fourth conduit 34. The amount of escaped polymer particles and liquid and/or gaseous diluents ranges from about 0 volume % to about 30 volume %, preferably from about 0 volume % to about 10 volume %, and more preferably from about 0.5 volume % to about 5 volume %, based on the total volume of the components, after settling, within the product chamber tank 22.

Opening the third valve 64 permits the solid polymer product to fall or otherwise be moved via the third conduit 26 and into the product blow tank 28. The contents of the product blow tank 28 may be permitted to settle or equalize by closing the third valve 64 and keeping closed a fifth valve 68 and a sixth valve 70. During settling the polymer particles will tend to fall to the bottom of the product blow tank 28, while the fluid unreacted material will tend to rise to the top of the product blow tank 28. In an alternate embodiment, two product blow tanks may be operated in sequence. In another embodiment, two pairs of blow tanks may be operated in sequence. The settling or equalization time varies from about 1 second to about 5 minutes, preferably from about 1 second to about 1.5 minutes, and more preferably from about 1 second to about 1 minute. The fifth valve 68 is then opened, and a large portion of the polymer particles, a large portion of the liquid and/or gaseous diluents, and any escaped gaseous monomers are transferred via a fifth conduit 44 into a product purge bin (not shown). Within the product purge bin, the polymer particles, liquid and/or gaseous diluents, and escaped gaseous monomers may be further separated. In one embodiment, this separation process includes the use of a compressor and/or condenser to recycle any escaped gaseous monomer. A large portion of the gaseous monomer within the product blow tank 28 is pulled through the sixth conduit 40 by the ejector 50. The fourth conduit 34 and the sixth conduit 40 may optionally be combined.

In one embodiment, about 50 volume % to about 100 volume %, preferably about 75 volume % to about 100 volume %, more preferably about 90 volume % to about 100 volume %, and most preferably about 95 volume % to about 100 volume % of the gaseous monomer within the product blow tank 28 is pulled through the sixth conduit 40 and the sixth valve 70 by the ejector 50. Further, polymer particles and liquid and/or gaseous diluents may escape from the product blow tank 28 into the sixth conduit 40. The amount of escaped polymer particles and liquid and/or gaseous diluents ranges from about 0 volume % to about 20 volume %, preferably from about 0 volume % to about 10 volume %, and more preferably from about 0.5 volume % to about 5 volume %, based on the total volume of the components, after settling, contained within the product blow tank 28.

The ejector 50 may be any gas phase ejector capable of being driven by high pressure olefin and pulling lower pressure olefin from at least one tank. Without intending to be limited by this disclosure, suitable ejectors include any device capable of pulling a stream of gaseous olefin using high-pressure gaseous olefin as a motive fluid. Suitable gas phase ejectors are generally available from, inter alia, Fox Valve Development Corporation located in Dover, N.J. and from Graham Corporation located in Houston, Tex. The ejector 50 is fed high-pressure olefin through the seventh conduit 54, and a seventh valve 72. The seventh valve 72 is used to regulate the flux of high pressure olefin fed into the process. In alternate embodiments, two or more ejectors may be operated, and in a still further embodiment the number of ejectors is equal to the number of the total tanks. The high pressure olefin is the same as one of the olefins that is circulated within the reactor 14. In one embodiment, the pressure of the high-pressure olefin entering the ejector through the seventh conduit 54 ranges from about 3600 kPag to about 8500 kPag, from about 4000 kPag to about 7500 kPag, or from about 4200 kPag to about 6000 kPag. In a further embodiment, the pressure of the olefin leaving the ejector through an eighth conduit 58 is sufficiently higher than the pressure of the reactor such that the gas flows from the ejector into the reactor. The high-pressure olefin, gaseous monomer, escaped liquid and/or gaseous diluents, and escaped polymer particles are transferred through the eighth conduit 58 and an eighth valve 74 from the ejector 50 into the bottom of the reactor. The eighth valve 74 is used to regulate the flux of material fed into the reactor 14 via the eighth conduit 58.

In another embodiment, the present invention provides methods of retrofitting an existing separation system. The specific method of retrofitting will depend on the configuration of the existing separation system. In general, however, the method of retrofitting comprises effectively limiting the compressor of the previous system. As used herein, the term "effectively limiting" means reducing, removing, effectively reducing, or effectively removing. For example, a compressor is effectively limited if it is a) removed from a system, b) replaced by a compressor with a lower duty, c) designed around by adding piping to direct the flow around the compressor, d) turned off so that the compressor acts as a valve and/or pipe, or e) any similarly reasonable engineering design changes. The method of retrofitting further comprises providing an ejector, which is driven by a high-pressure gaseous olefin, vacuuming at least a first portion of an effluent stream from at least one tank into the ejector, and recycling the vacuumed portion of the effluent stream from the ejector to a fluidized-bed reactor.

Figure 2:
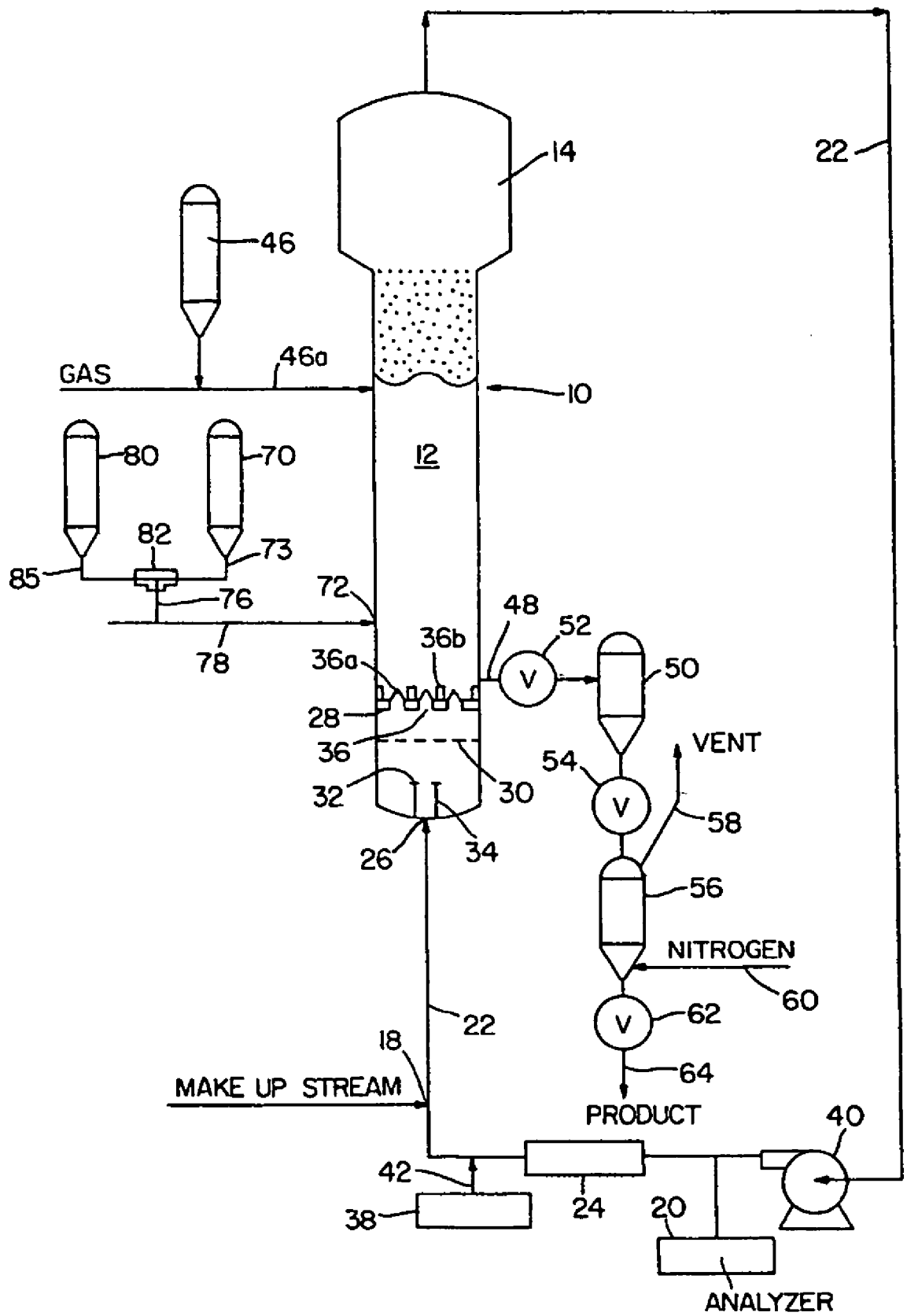
FIG. 2 illustrates FIG. 1 of U.S. Pat. No. 5,616,661, which is used as an aid to describe a prophetic example of one embodiment of a method of retrofitting an existing apparatus.

As a prophetic example, if the existing separation system is as disclosed in U.S. Pat. No. 5,616,661 (hereinafter "'661"), retrofitting may be accomplished as follows. With reference to FIG. 1 of '661, (now FIG. 2 in the instant invention) a first conduit is adapted to connect the reactor 10 at a location different from point 48 to the product discharge tank 50. Preferably, the first conduit is connected to the reactor 10 at a location near the plate 30. A second conduit is adapted to connect the product discharge tank 50 to an ejector (not shown). The venting means 58 is adapted to connect the product surge tank 56 to the ejector (not shown). Line 78 is disconnected from the reactor 10 and adapted to feed into the ejector (not shown). A third conduit is further adapted to connect the ejector (not shown) to the reactor 10.

In another embodiment, this invention relates to:

1. A method of separating unreacted monomer from a polymerization process effluent stream having unreacted monomer and polymer particles, the method comprising:
   a. passing the effluent stream of a fluidized-bed reactor into at least one container;
   b. feeding a first high-pressure olefin through an ejector; and
   c. vacuuming at least a portion of the effluent stream from the at least one container through the ejector.

2. The method of paragraph 1, further comprising recycling the vacuumed portion of the effluent stream from the ejector to the fluidized-bed reactor without the use of a mechanical compressor.

3. The method of paragraphs 1 or 2, wherein the vacuumed portion of the effluent stream comprises from about 50 weight percent to about 100 weight percent unreacted monomer.

4. The method of paragraphs 1 to 3, wherein the vacuumed portion of the effluent stream comprises from about 75 weight percent to about 100 weight percent unreacted monomer.

5. The method of paragraphs 1 to 4, wherein the vacuumed portion of the effluent stream comprises from about 90 weight percent to about 100 weight percent unreacted monomer.

6. The method of paragraphs 1 to 5, wherein the vacuumed portion of the effluent stream comprises from about 95 weight percent to about 100 weight percent unreacted monomer.

7. The method of paragraphs 1 to 6, wherein the unreacted monomer and high-pressure olefin are each selected from the group consisting of ethylene, propylene, ethylene containing alpha-olefin, and propylene containing alpha-olefin, wherein the alpha-olefin ranges from $C_1$ to $C_{10}$.

8. The method of paragraphs 1 to 7, wherein the unreacted monomer and high-pressure olefin are each ethylene or propylene.

9. The method of paragraphs 1 to 8, wherein the pressure of the high-pressure olefin is from about 3600 kPag to about 8500 kPag.

10. The method of paragraphs 1 to 9, wherein the at least one container comprises a product chamber tank.

11. The method of paragraphs 1 to 10, wherein the at least one container comprises a product blow tank.

12. The method of paragraphs 1 to 11, wherein the at least one container comprises a product chamber and a product blow tank.

13. The method of paragraphs 1 to 12, wherein the at least one container comprises at least two product chambers in parallel and at least two product blow tanks in parallel.

14. The method of paragraphs 1 to 13 further comprising:
   d. cycling a portion of the gaseous material contained within the reactor from an upper portion of the reactor to a lower portion of the reactor; and
   e. feeding a second high-pressure olefin into the reactor.

15. The method of paragraphs 1 to 14, wherein the second high-pressure olefin and the first high-pressure olefin are the same and are selected from the group consisting of ethylene, propylene, ethylene containing alpha-olefin, and propylene containing alpha-olefin, wherein the alpha-olefin ranges from $C_1$ to $C_{10}$.

16. The method of paragraphs 1 to 15, wherein the portion of gaseous material cycled from the upper portion of the reactor to a lower portion of the reactor is passed through a circulation unit.

17. A method of separating unreacted monomer from a polymerization process effluent stream having unreacted monomer and polymer particles, the method comprising:
   a. passing the effluent stream of a fluidized-bed reactor through a first conduit and a first valve into a product chamber tank;
   b. passing a first portion of the effluent stream from the product chamber tank through a second conduit and a second valve into a product blow tank;
   c. feeding a first high-pressure olefin into the inlet of an ejector, having an inlet, an outlet, and an alternate inlet port;
   d. vacuuming a second portion of the effluent stream from the product chamber tank through a third conduit and a third valve to the alternate inlet port of the ejector;
   e. vacuuming a third portion of the effluent stream from the product blow tank through a fourth conduit and a fourth valve to the alternate inlet port of the ejector;
   f. passing a fourth portion of the effluent stream from the product blow tank through a fifth conduit and a fifth valve to a product purge bin; and
   g. passing an exit stream from the outlet of the ejector into the fluidized-bed reactor.

18. The method of paragraph 17, further comprising allowing the effluent stream to equalize in the product chamber tank by closing the first valve, keeping the second valve and the third valve closed, and then allowing the first portion of the effluent stream to equalize in the product blow tank by closing the second valve, and keeping the fourth valve and the fifth valve closed.

19. The method of paragraphs 17 or 18, further comprising passing a fifth portion of the effluent stream from the product chamber tank into the fluidized-bed reactor.

20. The method of paragraphs 17 to 19, further comprising:
   h. separating the unreacted monomer in the product purge bin from the polymer particles; and
   i. recycling the unreacted monomer from the product purge bin to the fluidized-bed reactor.

21. The method of paragraphs 17 to 20, wherein the product purge bin comprise a nitrogen stripper and a compressor.

22. The method of paragraphs 18 to 21, wherein the effluent stream equalizes in the product chamber tank for about 1 second to about 10 minutes.

23. The method of paragraphs 18 to 22, wherein the effluent stream equalizes in the product chamber tank for about 1 second to about 5 minutes.

24. The method of paragraphs 18 to 23, wherein the effluent stream equalizes in the product chamber tank for from about 1 second to about 1 minute.

25. The method of paragraphs 18 to 24, wherein the effluent stream equalizes in the product chamber tank for about 1 second to about 30 seconds.

26. The method of paragraphs 18 to 25, wherein the first portion of the effluent stream equalizes in the product blow tank for about 1 second to about 5 minutes.

27. The method of paragraphs 18 to 26, wherein the first portion of the effluent stream equalizes in the product blow tank for about 1 second to about 1.5 minutes.

28. The method of paragraphs 17 to 27, wherein the effluent stream comprises from about 2 weight % to about 50 weight % unreacted monomer, from about 0 weight % to about 10 weight % diluent, and from about 40 weight % to about 98 weight % polymer.

29. The method of paragraphs 17 to 28, wherein the effluent stream comprises from about 2 weight % to about 20 weight % unreacted monomer, from about 0 weight % to about 10 weight % diluent, and from about 70 weight % to about 98 weight % polymer.

30. The method of paragraphs 17 to 29, wherein the first portion of the effluent stream comprises from about 2 weight % to about 50 weight % unreacted monomer, from about 0 weight % to about 10 weight % diluent, and from about 40 weight % to about 98 weight % polymer.

31. The method of paragraphs 17 to 30, wherein the first portion of the effluent stream comprises from about 2 weight % to about 20 weight % unreacted monomer, from about 0 weight % to about 10 weight % diluent, and from about 70 weight % to about 98 weight % polymer.

32. The method of paragraphs 17 to 31, wherein the second portion of the effluent stream comprises from about 2 weight % to about 50 weight % unreacted monomer, from about 0 weight % to about 10 weight % diluent, and from about 40 weight % to about 98 weight % polymer.

33. The method of paragraphs 17 to 32, wherein the second portion of the effluent stream comprises from about 2 weight % to about 20 weight % unreacted monomer, from about 0 weight % to about 10 weight % diluent, and from about 70 weight % to about 98 weight % polymer.

34. The method of paragraphs 17 to 33, wherein the third portion of the effluent stream comprises from about 2 weight % to about 50 weight % unreacted monomer, from about 0 weight % to about 10 weight % diluent, and from about 40 weight % to about 98 weight % polymer.

35. The method of paragraphs 17 to 34, wherein the third portion of the effluent stream comprises from about 2 weight % to about 20 weight % unreacted monomer, from about 0 weight % to about 10 weight % diluent, and from about 70 weight % to about 98 weight % polymer.

36. The method of paragraphs 17 to 35, wherein the fourth portion of the effluent stream comprises from about 2 weight % to about 50 weight % unreacted monomer, from about 0 weight % to about 10 weight % diluent, and from about 40 weight % to about 98 weight % polymer.

37. The method of paragraphs 17 to 36, wherein the fourth portion of the effluent stream comprises from about 2 weight % to about 20 weight % unreacted monomer, from about 0 weight % to about 10 weight % diluent, and from about 70 weight % to about 98 weight % polymer.

38. The method of paragraphs 17 to 37, wherein the unreacted monomer and high-pressure olefin are each selected from the group consisting of ethylene, propylene, ethylene containing alpha-olefin, and propylene containing alpha-olefin, wherein the alpha-olefin ranges from $C_1$ to $C_{10}$.

39. The method of paragraphs 17 to 38, wherein the unreacted monomer and high-pressure olefin are each ethylene or propylene.

40. The method of paragraphs 17 to 39, further comprising:
   h. cycling a portion of the unreacted monomer from an upper portion of the reactor to a lower portion of the reactor; and
   i. feeding a second high-pressure olefin into the reactor.

41. The method of paragraph 40, wherein the second high-pressure olefin and the first high-pressure olefin are the same and are selected from the group consisting of ethylene, propylene, ethylene containing alpha-olefin, and propylene containing alpha-olefin, wherein the alpha-olefin ranges from $C_1$ to $C_{10}$.

42. The method of paragraphs 40 or 41, wherein the portion of unreacted monomer cycled from the upper portion of the reactor to a lower portion of the reactor is passed through a circulation unit.

43. An apparatus for separating unreacted monomer from a polymerization process effluent stream comprising:
   a. a fluidized-bed reactor having a first conduit and a first valve connected to a first tank; and
   b. an ejector having a second conduit and a second valve connected to the first tank and a third conduit and a third valve connected to the fluidized-bed reactor.

44. The apparatus of paragraph 43 further comprising:
   c. a fourth conduit and a fourth valve connected from the fluidized-bed reactor to the first tank;
   d. a second tank having a fifth conduit and a fifth valve connected to the first tank;
   e. a sixth conduit and a sixth valve connected to the ejector (from second tank);
   f. a seventh conduit and a seventh valve connecting an upper portion of the reactor to a lower portion of the reactor; and
   g. an eighth conduit and an eighth valve connecting a supply of fresh monomer to the reactor.

45. The apparatus of paragraphs 43 or 44 further comprising a ninth conduit and a ninth valve connected to a product purge bin.

46. The apparatus of paragraphs 43 to 45, wherein the third conduit and the sixth conduit are connected.

47. A method of retrofitting an existing polymerization process comprising:
   a. effectively limiting a compressor;
   b. vacuuming at least a first portion of an effluent stream from at least one tank into an ejector, wherein the ejector is driven by a high-pressure gaseous olefin; and
   c. recycling the vacuumed portion of the effluent stream from the ejector to a fluidized-bed reactor.

48. The method of paragraph 46 further comprising:
   d. vacuuming a second portion of the effluent stream from a second tank into the ejector.

The present invention provides a method of separating unreacted monomer from a polymerization process effluent stream having unreacted monomer and polymer particles. The method comprises passing the effluent stream of a fluidized-bed reactor into at least one container; feeding a first high-pressure olefin through an ejector; and vacuuming at least a portion of the effluent stream from the at least one container through the ejector.

In some embodiments of the present invention, the method further comprises recycling the vacuumed portion of the effluent stream from the ejector to the fluidized-bed reactor without the use of a mechanical compressor. The vacuumed portion of the effluent stream generally comprises from about 50 weight percent to about 100 weight percent unreacted monomer, preferably from about 75 weight percent to about 100 weight percent unreacted monomer, more preferably from about 90 weight percent to about 100 weight percent unreacted monomer, and still more preferably from about 95 weight percent to about 100 weight percent unreacted monomer. In further embodiments, the unreacted monomer and high-pressure olefin are each selected from the group consisting of ethylene, propylene, ethylene containing alpha-olefin, and propylene containing alpha-olefin, wherein the alpha-olefin ranges from $C_1$ to $C_{10}$. Optionally, the unreacted monomer and high-pressure olefin each are ethylene. Optionally, the unreacted monomer and high-pressure olefin each are propylene. The pressure of the high-pressure olefin typically ranges from about 3600 kPag to about 8500 kPag. Further, the at least one container optionally comprises a product chamber tank, a product blow tank, two or more product chambers in parallel, or two or more product blow tanks in parallel, or any combination of the foregoing, such as, for example, a product chamber and a product blow tank. In some embodiments, the method further comprises cycling a portion of the gaseous material contained within the reactor from an upper portion of the reactor to a lower portion of the reactor and feeding a second high-pressure olefin into the reactor. The second high-pressure olefin and the first high-pressure olefin may be different or the same, and are each selected from the group consisting of ethylene, propylene, ethylene containing alpha-olefin, and propylene containing alpha-olefin, wherein the alpha-olefin ranges from $C_1$ to $C_{10}$. The portion of gaseous material cycled from the upper portion of the reactor to a lower portion of the reactor may optionally be passed through a circulation unit.

In another embodiment, the present invention provides a method of separating unreacted monomer from a polymerization process effluent stream having unreacted monomer and polymer particles. The method comprises passing the effluent stream of a fluidized-bed reactor through a first conduit and a first valve into a product chamber tank; passing a first portion of the effluent stream from the product chamber tank through a second conduit and a second valve into a product blow tank; feeding a first high-pressure olefin into the inlet of an ejector, having an inlet, an outlet, and an alternate inlet port; vacuuming a second portion of the effluent stream from the product chamber tank through a third conduit and a third valve to the alternate inlet port of the ejector; vacuuming a third portion of the effluent stream from the product blow tank through a fourth conduit and a fourth valve to the alternate inlet port of the ejector; passing a fourth portion of the effluent stream from the product blow tank through a fifth conduit and a fifth valve to a product purge bin; and passing an exit stream from the outlet of the ejector into the fluidized-bed reactor.

In some embodiments, the effluent stream is allowed to equalize in the product chamber tank by closing the first valve and keeping the second valve and the third valve closed. The portion of the effluent stream in the product blow tank may also be allowed to equalize by closing the second valve and keeping the fourth valve and the fifth valve closed. When the effluent stream is allowed to equalize in the product chamber tank, the equalization period is from about 1 second to about 10 minutes, preferably from about 1 second to about 5 minutes, more preferably from about 1 second to about 1 minute, most preferably from about 1 second to about 30 seconds. Further, the equalization period for the first portion of the effluent stream in the product blow tank is from about 1 second to about 5 minutes, preferably from about 1 second to about 1.5 minutes.

In further embodiments, the method also comprises passing a fifth portion of the effluent stream from the product chamber into the product purge bin. The unreacted monomer in the product purge bin may additionally be separated from the polymer particles and the unreacted monomer may be recycled from the product purge bin to the fluidized-bed reactor. Additionally, the product purge bin optionally comprises a nitrogen stripper and a compressor.

The effluent stream typically comprises from about 2 weight % to about 50 weight % unreacted monomer, from about 0 weight % to about 10 weight % diluent, and from about 40 weight % to about 98 weight % polymer; preferably from about 2 weight % to about 20 weight % unreacted monomer, from about 0 weight % to about 10 weight % diluent, and from about 70 weight % to about 98 weight % polymer. Further, the first portion of the effluent stream which is passed into the product blow tank typically comprises from about 2 weight % to about 50 weight % unreacted monomer, from about 0 weight % to about 10 weight % diluent, and from about 40 weight % to about 98 weight % polymer; preferably from about 2 weight % to about 20 weight % unreacted monomer, from about 0 weight % to about 10 weight % diluent, and from about 70 weight % to about 98 weight % polymer. The second portion of effluent stream, which is vacuumed from the product chamber through the ejector, typically comprises from about 2 weight % to about 50 weight % unreacted monomer, from about 0 weight % to about 10 weight % diluent, and from about 40 weight % to about 98 weight % polymer; preferably from about 2 weight % to about 20 weight % unreacted monomer, from about 0 weight % to about 10 weight % diluent, and from about 70 weight % to about 98 weight % polymer. The third portion of effluent stream, which is vacuumed from the product blow tank through the ejector, typically comprises from about 2 weight % to about 50 weight % unreacted monomer, from about 0 weight % to about 10 weight % diluent, and from about 40 weight % to about 98 weight % polymer; preferably from about 2 weight % to about 20 weight % unreacted monomer, from about 0 weight % to about 10 weight % diluent, and from about 70 weight % to about 98 weight % polymer. The fourth portion of effluent stream, passed from the product blow tank to the product purge bin, typically comprises from about 2 weight % to about 50 weight % unreacted monomer, from about 0 weight % to about 10 weight % diluent, and from about 40 weight % to about 98 weight % polymer; preferably from about 2 weight % to about 20 weight % unreacted monomer, from about 0 weight % to about 10 weight % diluent, and from about 70 weight % to about 98 weight % polymer.

In some embodiments of the present invention, the unreacted monomer and high-pressure olefin are each selected from the group consisting of ethylene, propylene, ethylene containing alpha-olefin, and propylene containing alpha-olefin, wherein the alpha-olefin ranges from $C_1$ to $C_{10}$ (such as butene, pentene, hexane, heptene, octane, nonene, and decene). Optionally, the unreacted monomer and high-pressure olefin are each ethylene. Optionally, the unreacted monomer and high-pressure olefin are each propylene. The second high-pressure olefin and the first high-pressure olefin may be the same or different and are each selected from the group consisting of ethylene, propylene, ethylene containing alpha-olefin, and propylene containing alpha-olefin, wherein the alpha-olefin ranges from $C_1$ to $C_{10}$ (such as butene, pentene, hexane, heptene, octane, nonene, and decene). The portion of gaseous material cycled from the upper portion of the reactor may optionally be passed to a lower portion of the reactor through a circulation unit.

In a further embodiment, the present invention provides an apparatus for separating unreacted monomer from a polymerization process effluent stream, wherein the apparatus comprises a fluidized-bed reactor having a first conduit and a first valve connected to a first tank, an ejector having a second conduit and a second valve connected to the first tank, and a third conduit and a third valve connected to the fluidized-bed reactor.

In some embodiments, the apparatus may further comprise a fourth conduit and a fourth valve connected from the fluidized-bed reactor to the first tank, a second tank having a fifth conduit and a fifth valve connected to the first tank, a sixth conduit and a sixth valve connected to the ejector, a seventh conduit and a seventh valve connecting an upper portion of the reactor to a lower portion of the reactor, and an eighth conduit and an either valve connecting a supply of fresh monomer to the reactor. The method may further comprise a ninth conduit and a ninth valve connected to a product purge bin. Further, the third conduit and the sixth conduit are optionally connected.

In a still further embodiment, the present invention provides a method for retrofitting a polymerization process. The process having at least a fluidized bed reactor, an effluent stream comprising unreacted monomer and polymer particles, one or more product tanks, and a compressor. The method comprises effectively limiting the compressor; vacuuming at least a first portion of the effluent stream from the at least one tank into an ejector, wherein the ejector is driven by a high-pressure gaseous olefin; and recycling the vacuumed portion of the effluent stream from the ejector to a fluidized-bed reactor. In some embodiments, a second portion of the effluent stream is vacuumed from a second tank into the ejector.

The foregoing description is presented to explain the present invention and its practical application and to thereby enable those skilled in the art to make and utilize the invention. However, this description is for the purpose of illustration and example only, and is not intended to be exhaustive or to limit the invention to the precise form disclosed. Those skilled in the art will recognize that many modifications and variations are possible in light of the above teaching without departing from the spirit and scope of the following claims. All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A method of separating unreacted monomer from a polymerization process effluent stream having unreacted monomer and polymer particles, the method comprising:
   a. passing the effluent stream of a fluidized-bed reactor into at least one container;
   b. feeding a first high-pressure olefin through an ejector;
   c. vacuuming at least a portion of the effluent stream from the at least one container through the ejector; and
   d. recycling the vacuumed portion of the effluent stream from the ejector to the fluidized-bed reactor without the use of a mechanical compressor, wherein the vacuumed portion of the effluent stream comprises from about 50 weight percent to about 100 weight percent unreacted monomer.

2. The method of claim 1, wherein the vacuumed portion of the effluent stream comprises from about 75 weight percent to about 100 weight percent unreacted monomer.

3. The method of claim 2, wherein the vacuumed portion of the effluent stream comprises from about 90 weight percent to about 100 weight percent unreacted monomer.

4. The method of claim 3, wherein the vacuumed portion of the effluent stream comprises from about 95 weight percent to about 100 weight percent unreacted monomer.

5. The method of claim 1, wherein the unreacted monomer and high-pressure olefin are each selected from the group consisting of ethylene, propylene, ethylene containing alpha-olefin, and propylene containing alpha-olefin, wherein the alpha-olefin ranges from $C_1$ to $C_{10}$.

6. The method of claim 5, wherein the unreacted monomer and high-pressure olefin are each propylene.

7. The method of claim 1, wherein the pressure of the high-pressure olefin is from about 3600 kPag to about 8500 kPag.

8. The method of claim 1, wherein the at least one container comprises a product chamber tank.

9. The method of claim 1, wherein the at least one container comprises a product blow tank.

10. The method of claim 1, wherein the at least one container comprises a product chamber and a product blow tank.

11. The method of claim 1, wherein the at least one container comprises at least two product chambers in parallel and at least two product blow tanks in parallel.

12. The method of claim 1, further comprising:
   d. cycling a portion of the gaseous material contained within the reactor from an upper portion of the reactor to a lower portion of the reactor; and
   e. feeding a second high-pressure olefin into the reactor.

13. The method of claim 12, wherein the second high-pressure olefin and the first high-pressure olefin are the same and are selected from the group consisting of ethylene, propylene, ethylene containing alpha-olefin, and propylene containing alpha-olefin, wherein the alpha-olefin ranges from $C_1$ to $C_{10}$.

14. The method of claim 12, wherein the portion of gaseous material cycled from the upper portion of the reactor to a lower portion of the reactor is passed through a circulation unit.

15. A method of separating unreacted monomer from a polymerization process effluent stream having unreacted monomer and polymer particles, the method comprising:
   a. passing the effluent stream of a fluidized-bed reactor through a first conduit and a first valve into a product chamber tank;
   b. passing a first portion of the effluent stream from the product chamber tank through a second conduit and a second valve into a product blow tank;
   c. feeding a first high-pressure olefin into the inlet of an ejector, having an inlet, an outlet, and an alternate inlet port;
   d. vacuuming a second portion of the effluent stream from the product chamber tank through a third conduit and a third valve to the alternate inlet port of the ejector;
   e. vacuuming a third portion of the effluent stream from the product blow tank through a fourth conduit and a fourth valve to the alternate inlet port of the ejector;
   f. passing a fourth portion of the effluent stream from the product blow tank through a fifth conduit and a fifth valve to a product purge bin; and
   g. passing an exit stream from the outlet of the ejector into the fluidized-bed reactor.

16. The method of claim 15, further comprising allowing the effluent stream to equalize in the product chamber tank by closing the first valve, the second valve, and the third valve, and then allowing the first portion of the effluent stream to equalize in the product blow tank by closing the second valve, the fourth valve, and the fifth valve.

17. The method of claim 15, further comprising passing a fifth portion of the effluent stream from the product chamber tank into the fluidized-bed reactor.

18. The method of claim 15, further comprising:
   h. separating the unreacted monomer in the product purge bin from the polymer particles; and
   i. recycling the unreacted monomer from the product purge bin to the fluidized-bed reactor.

19. The method of claim 18, wherein the product purge bin comprises a compressor and a nitrogen stripper.

20. The method of claim 16, wherein the effluent stream equalizes in the product chamber tank for about 1 second to about 10 minutes.

21. The method of claim 20, wherein the effluent stream equalizes in the product chamber tank for about 1 second to about 5 minutes.

22. The method of claim 21, wherein the effluent stream equalizes in the product chamber tank for from about 1 second to about 1 minute.

23. The method of claim 22, wherein the effluent stream equalizes in the product chamber tank for about 1 second to about 30 seconds.

24. The method of claim 16, wherein the first portion of the effluent stream equalizes in the product blow tank for about 1 second to about 5 minutes.

25. The method of claim 24, wherein the first portion of the effluent stream equalizes in the product blow tank for about 1 second to about 1.5 minutes.

26. The method of claim 15, wherein the effluent stream comprises from about 2 weight % to about 50 weight % unreacted monomer, from about 0 weight % to about 10 weight % diluent, and from about 40 weight % to about 98 weight % polymer.

27. The method of claim 26, wherein the effluent stream comprises from about 2 weight % to about 20 weight % unreacted monomer, from about 0 weight % to about 10 weight % diluent, and from about 70 weight % to about 98 weight % polymer.

28. The method of claim 15, wherein the first portion of the effluent stream comprises from about 2 weight % to about 50 weight % unreacted monomer, from about 0 weight % to about 10 weight % diluent, and from about 40 weight % to about 98 weight % polymer.

29. The method of claim 28, wherein the first portion of the effluent stream comprises from about 2 weight % to about 20 weight % unreacted monomer, from about 0 weight % to about 10 weight % diluent, and from about 70 weight % to about 98 weight % polymer.

30. The method of claim 15, wherein the second portion of the effluent stream comprises from about 2 weight % to about 50 weight % unreacted monomer, from about 0 weight % to about 10 weight % diluent, and from about 40 weight % to about 98 weight % polymer.

31. The method of claim 30, wherein the second portion of the effluent stream comprises from about 2 weight % to about 20 weight % unreacted monomer, from about 0 weight % to about 10 weight % diluent, and from about 70 weight % to about 98 weight % polymer.

32. The method of claim 15, wherein the third portion of the effluent stream comprises from about 2 weight % to about 50 weight % unreacted monomer, from about 0 weight % to about 10 weight % diluent, and from about 40 weight % to about 98 weight % polymer.

33. The method of claim 32, wherein the third portion of the effluent stream comprises from about 2 weight % to about 20 weight % unreacted monomer, from about 0 weight % to about 10 weight % diluent, and from about 70 weight % to about 98 weight % polymer.

34. The method of claim 15, wherein the fourth portion of the effluent stream comprises from about 2 weight % to about 50 weight % unreacted monomer, from about 0 weight % to about 10 weight % diluent, and from about 40 weight % to about 98 weight % polymer.

35. The method of claim 34, wherein the fourth portion of the effluent stream comprises from about 2 weight % to about 20 weight % unreacted monomer, from about 0 weight % to about 10 weight % diluent, and from about 70 weight % to about 98 weight % polymer.

36. The method of claim 15, wherein the unreacted monomer and high-pressure olefin are each selected from the group consisting of ethylene, propylene, ethylene containing alpha-olefin, and propylene containing alpha-olefin, wherein the alpha-olefin ranges from $C_1$ to $C_{10}$.

37. The method of claim 36, wherein the unreacted monomer and high-pressure olefin are each propylene.

38. The method of claim 15, further comprising:
   h. cycling a portion of the unreacted monomer from an upper portion of the reactor to a lower portion of the reactor; and
   i. feeding a second high-pressure olefin into the reactor.

39. The method of claim 38, wherein the second high-pressure olefin and the first high-pressure olefin are the same and are selected from the group consisting of ethylene, propylene, ethylene containing alpha-olefin, and propylene containing alpha-olefin, wherein the alpha-olefin ranges from $C_1$ to $C_{10}$.

40. The method of claim 38, wherein the portion of unreacted monomer cycled from the upper portion of the reactor to a lower portion of the reactor is passed through a circulation unit.

* * * * *